(12) United States Patent
Lee

(10) Patent No.: US 9,907,390 B2
(45) Date of Patent: Mar. 6, 2018

(54) PORTABLE INTERDENTAL TOOTHBRUSH

(71) Applicant: Sang Geun Lee, Gwangju-si (KR)

(72) Inventor: Sang Geun Lee, Gwangju-si (KR)

( * ) Notice: Subject to any disclaimer, the term of this patent is extended or adjusted under 35 U.S.C. 154(b) by 0 days.

(21) Appl. No.: 14/904,724

(22) PCT Filed: Apr. 14, 2015

(86) PCT No.: PCT/KR2015/003624
§ 371 (c)(1),
(2) Date: Jan. 13, 2016

(87) PCT Pub. No.: WO2016/035961
PCT Pub. Date: Mar. 10, 2016

(65) Prior Publication Data
US 2017/0164726 A1  Jun. 15, 2017

(30) Foreign Application Priority Data

Sep. 2, 2014 (KR) .......................... 10-2014-0116309
Nov. 18, 2014 (KR) .......................... 10-2014-0161064

(51) Int. Cl.
*A61C 15/00* (2006.01)
*A46B 11/00* (2006.01)
*A46B 9/04* (2006.01)

(52) U.S. Cl.
CPC ............ *A46B 11/0024* (2013.01); *A46B 9/04* (2013.01); *A46B 11/0086* (2013.01); *A61C 15/00* (2013.01); *A46B 2200/108* (2013.01)

(58) Field of Classification Search
CPC .. A46B 11/0013; A46B 11/0041; A61C 15/00

USPC .......................................... 401/278, 284, 286
See application file for complete search history.

(56) References Cited

U.S. PATENT DOCUMENTS

| 4,828,420 | A  | * | 5/1989 | Otsuka | ...................... | A46B 7/04 132/329 |
| 7,232,310 | B2 | * | 6/2007 | Han | .......................... | A46B 7/04 401/290 |
| 7,699,608 | B2 | * | 4/2010 | Han | .......................... | A46B 3/18 433/80 |
| 8,657,518 | B2 | * | 2/2014 | Han | ...................... | A46B 5/0095 15/167.1 |
| 9,022,680 | B1 | * | 5/2015 | Lubyanitskiy | ..... | A46B 11/0086 401/142 |

(Continued)

FOREIGN PATENT DOCUMENTS

| KR | 20-0246271 | 10/2001 |
| KR | 10-0468075 | 1/2005 |

(Continued)

OTHER PUBLICATIONS

English Translation of 10-2008-0100531.

(Continued)

*Primary Examiner* — David Walczak
*Assistant Examiner* — Joshua Wiljanen
(74) *Attorney, Agent, or Firm* — KORUS Patent, LLC; Seong Il Jeong

(57) ABSTRACT

The portable interdental toothbrush according to the present invention has a simple structure enabling mass production at a low cost, thereby allowing consumers to use at a low price, which promotes the dental and oral health for citizens.

4 Claims, 13 Drawing Sheets

(56) References Cited

U.S. PATENT DOCUMENTS

2007/0006402 A1   1/2007  Kang
2013/0130196 A1*  5/2013  Joyashiki ............... A61C 15/00
                                                    433/87

FOREIGN PATENT DOCUMENTS

| KR | 10-2006-0060009 | 6/2006 |
| KR | 10-2007-0074304 | 7/2007 |
| KR | 10-2008-0100531 | 11/2008 |
| KR | 20-2012-0007150 | 10/2012 |
| KR | 20-0465554 | 2/2013 |

OTHER PUBLICATIONS

English Translation of 20-0246271.
English Translation of 20-2012-0007150.
English Translation of 10-0468075.
English Translation of 10-2007-0074304.
English Translation of 10-2006-0060009.
English Translation of 20-0465554.

* cited by examiner

PORTABLE INTERDENTAL TOOTHBRUSH

CROSS-REFERENCE TO RELATED APPLICATION(S)

This application claims the benefit of International Application No. PCT/KR2015/003624, filed on Apr. 14, 2015, based on Korean Patent Application No. 10-2014-0116309, filed on Sep. 2, 2014, and Korean Patent Application No. 10-2014-0161064, filed on Nov. 18, 2014 the disclosures of which are hereby incorporated by reference herein in their entirety.

BACKGROUND

1. Technical Field

The present invention relates to a portable interdental toothbrush and is more particularly concerned with a portable interdental toothbrush which can be carded for portable use during travel or outing so as to clean and sterilize foreign materials and plaque that fit between teeth after meals, wherein a fixing portion of the brush body is inserted and assembled into the discharge hole of a cleaning solution tube filled with a cleaning solution, thereby the portable interdental toothbrush is very easily manufactured, its use is convenient, its configuration is simple, manufacturing cost is low, mass production is possible and it can be provided at a low price, thus promoting the dental and oral health for citizens.

2. Description of the Related Art

In general, the interdental toothbrush has small brush-shaped bristles for cleaning spaces between the teeth mounted on the end of the handle. They are orally hygiene instruments used to clean the oral cavity by washing interdental spaces using putting in and pulling out motions of the brush in the interdental space gaps. Use of the interdental toothbrush facilitates removal of food-residue and plaque of hard-to-reach areas of usual toothbrushes, sterilization after dental treatment such as scaling, prevention of plaque after smoking, and cleaning of orthodontic instruments such as braces to maintain oral hygiene.

However, looking at the actual state of use of the current interdental brush, there are problems that the cleaning is conducted only using the brush and thus gums become stimulated, bleeding occurs frequently and the ability to remove food-residue and plaque becomes insufficient. Further, if interdental brushes are continuously used, them is an unpleasant smell from the brush due to a bad cleanliness, particularly, the growth of bacteria.

In an attempt to solve the above-mentioned problems, as shown in FIG. 1, there has been developed a toothbrush in which a lid 120 containing a cleaning solution 140 is coupled inside the toothbrush 110 coupled with bristles 130, and each time the user uses it, the toothbrush 110 is immersed in the cleaning solution so that the toothbrush 110 is soaked with the cleaning solution 130. However, this method has disadvantages in that the cleaning solution 140 is stored in the lid 120 of the toothbrush 110 and thus the cleaning solution can be discharged outside if the lid 120 is open due to the user's carelessness. Also, care should be taken for preventing loss of the cleaning solution stored in the lid 120 when using the toothbrush 110. Further, it is troublesome to repeat the motions of putting in and pulling out the toothbrush 110 in the lid 120 every time the user tries to soak the toothbrush 110 in the cleaning solution.

To solve the above problems, Korean Patent No. 10-0468075 titled "An interdental toothbrush provided with a cleaning solution" has been suggested. The interdental toothbrush disclosed in this patent comprises, as shown in FIG. 2, a case 40 having both ends opened, a storage tank 30 installed in the case 40, on one side of which is formed a discharge hole 32, and the other side of which is open, a pleated tube 70 coupled to the opened outer circumferential face of the storage tank 30 and to a check valve 80 joined to an end thereof, a spring 55 installed on the outer circumferential face of the discharge hole 32, a coupling socket 50 installed on the outer circumferential face of the discharge hole 32 and having a screw part on the outer circumferential face thereof, a node 60 screw-coupled to the discharge hole 32, an end portion of which is splitted into upper and lower parts, and having a cone-shaped discharge hole inside and a slanted bump 62 on an outer circumferential face thereof, a fixing ring 65 coupled to the split outer circumferential face of the male 60 and contacted with a side surface of the coupling socket 50, and a nozzle cap 90 engaged in the screw portion formed on the coupling socket 50 and having a brush 95 assembled on the front surface thereof and a couple of injection holes 92 formed therein. This interdental toothbrush is effective in eliminating the inconvenience of handling cleaning solution of the prior art, however, the structure is complicated and the manufacturing cost is high, so it is not practical. Further, when the cleaning solution is all used up, the storage tank 30 should be replenished with a new cleaning solution, however, it is impossible to replenish the cleaning solution in the storage tank 30, which makes it impossible to continuously use the interdental toothbrush purchased at a high price.

SUMMARY

It is an object of the present invention to solve the above-described problems encountered with the prior arts and to provide a portable interdental toothbrush in which, when the fixing portion of the brush body is inserted into and assembled with the discharge hole of the cleaning solution tube while the cleaning solution is filled in the cleaning solution tube, the pressure difference between the cleaning solution-filled space and the atmospheric pressure is generated, thereby the cleaning solution is present in the filling space without discharging. By using these features, the portable interdental toothbrush is very easily manufactured, its use is convenient, the configuration is simple, manufacturing costs are low, mass production is possible and it can be provided at a low price, thus promoting the dental and oral health for citizens.

Another object of the present invention is to provide a portable interdental toothbrush, which is convenient to carry, and which ensures activity as well since the cleaning solution is received while sealed up tightly. The discharge of the cleaning solution can be controlled by the easy opening and shutting of the cleaning solution tubes assembly protrusion during use, in this way, it has a simple structure, low manufacturing cost, and convenience in use.

The above objects of the present invention is achieved by a portable interdental toothbrush according to the present invention having a structure in which a fixing portion of a blush body having the fixing portion on one end and a brush attached on the other end is press-fitted forcibly into a discharge hole of a cleaning solution tube having a filling space filled with a cleaning solution and the discharge hole for discharging the cleaning solution while the cleaning solution tube is filled with the cleaning solution and the cleaning solution is not discharged if any pressure is applied to an outer surface of the cleaning solution tube since the pressure applied to the cleaning solution filled in the filling space is lower than the atmospheric pressure.

The above objects of the present invention is achieved by a portable interdental toothbrush according to the present invention comprising a cleaning solution tube in which a cleaning solution is received to be carried conveniently and an assembly protrusion for discharging the cleaning solution is formed; a tube cover assembled to the assembly protrusion of the cleaning solution tube having an assembly hole into which the assembly protrusion of the cleaning solution tube is inserted and assembled in a lower pan and a fixing hole having a diameter larger than that of the assembly hole, in which a brush fixing portion installed with a brush on one end is inserted and fixed above the assembly hole; and a brush fixing portion which is inserted into the fixing hole of the tube cover and fixed, in which a contact end is formed on a lower end part to be closely contacted detachably to the assembly protrusion and the brush is fixed on the other end.

The portable interdental toothbrush according to the present invention has a simple structure to enable mass production at a low cost. Furthermore, it is convenient to use and carry. Also, the simple structure, easy manufacturing, and low manufacturing cost enables any user to use it, which promotes the dental and oral health for citizens.

BRIEF DESCRIPTION OF THE DRAWINGS

The above and other objects, features and advantages of the present invention will be more clearly understood from the following detailed description taken in conjunction with the accompanying drawings, in which.

DETAILED DESCRIPTION

Figure 1:
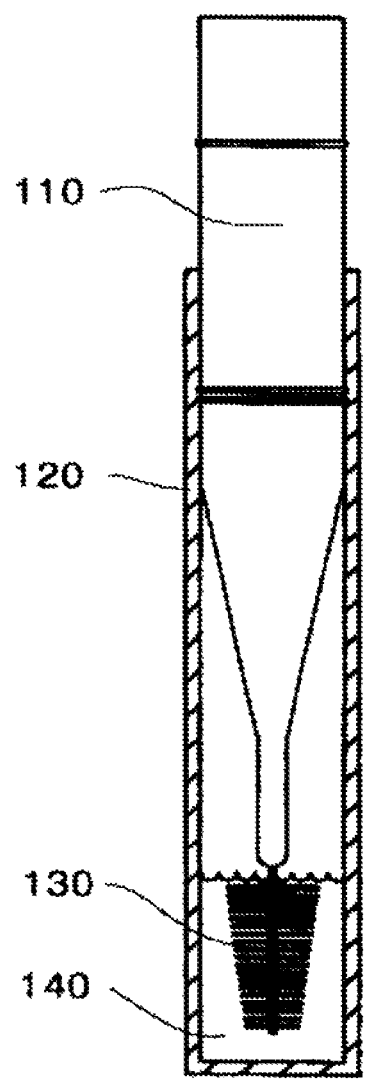
FIG. 1 is a schematic longitudinal cross-sectional view of a conventional interdental toothbrush.
Figure 2:
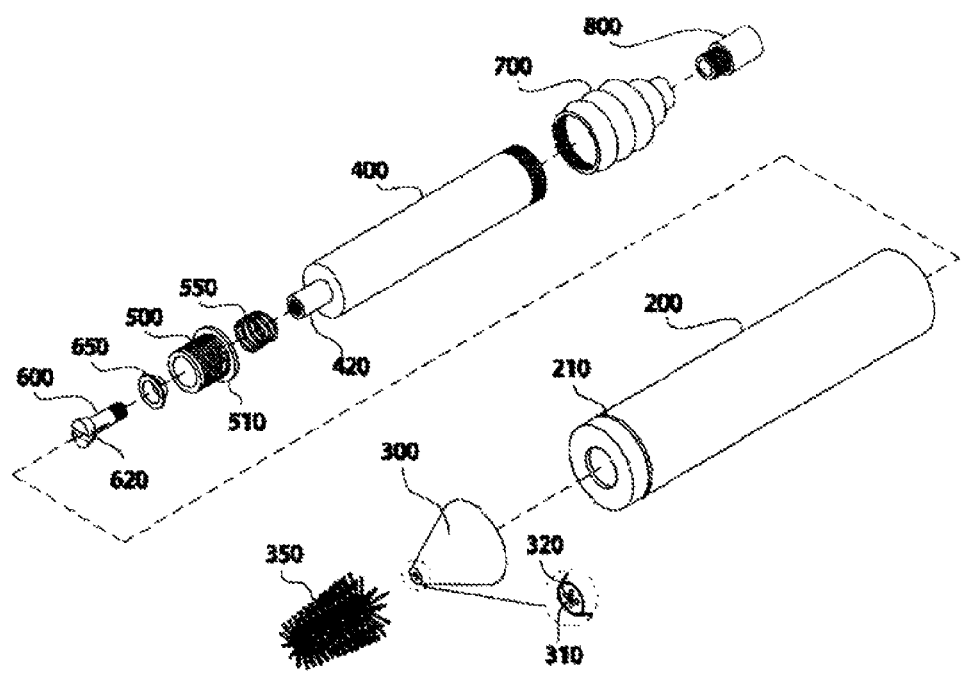
FIG. 2 is an exploded perspective view of another conventional interdental brush.

Hereinafter, the configuration and operation of preferred embodiments of the present invention will be described in detail with reference to the accompanying drawings. Here, in the case of assigning the reference numerals to the components of the drawings, it should be noted that with respect to the same components the same reference numerals are used even in different drawings.

Figure 3:
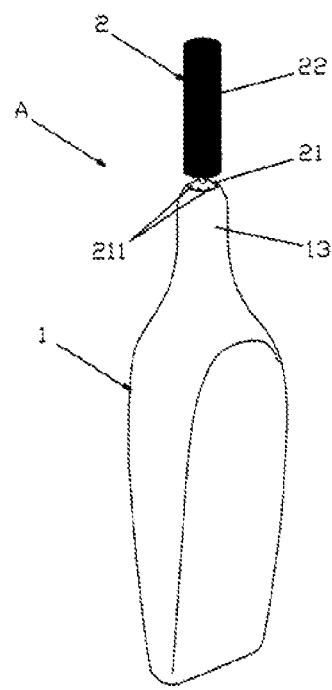
FIG. 3 is a perspective view of a portable interdental toothbrush in accordance with the first embodiment of the present invention.
Figure 4:
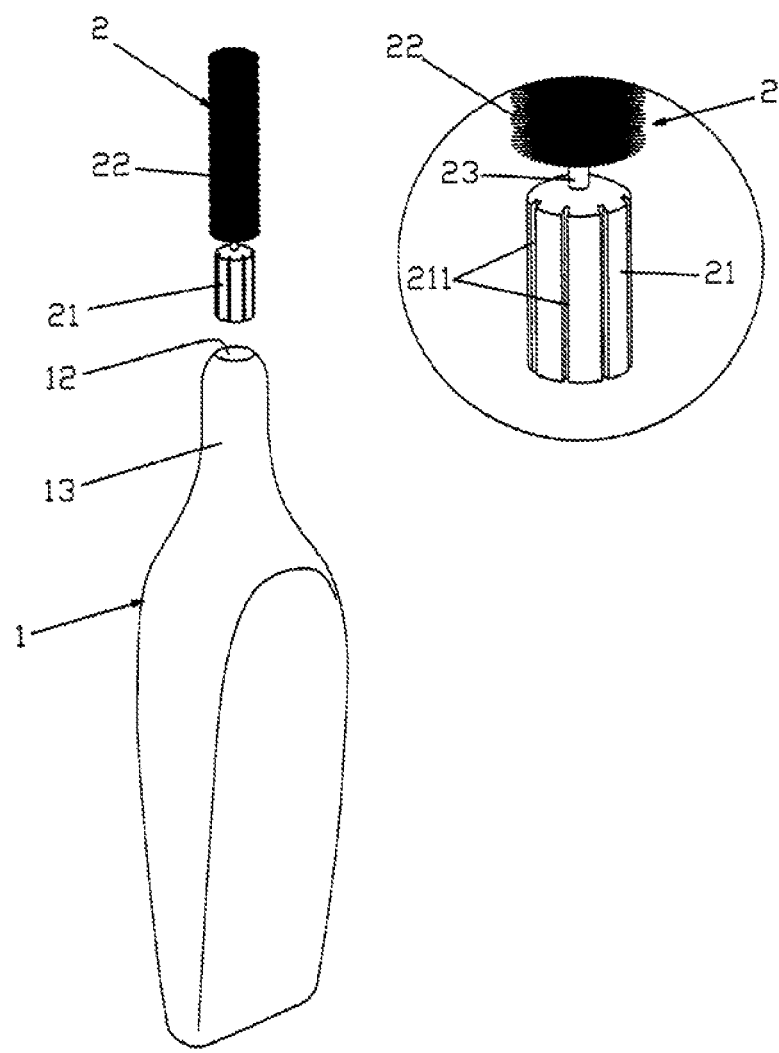
FIG. 4 is an exploded perspective view of a portable interdental toothbrush in accordance with the first embodiment of the present invention.
Figure 5:
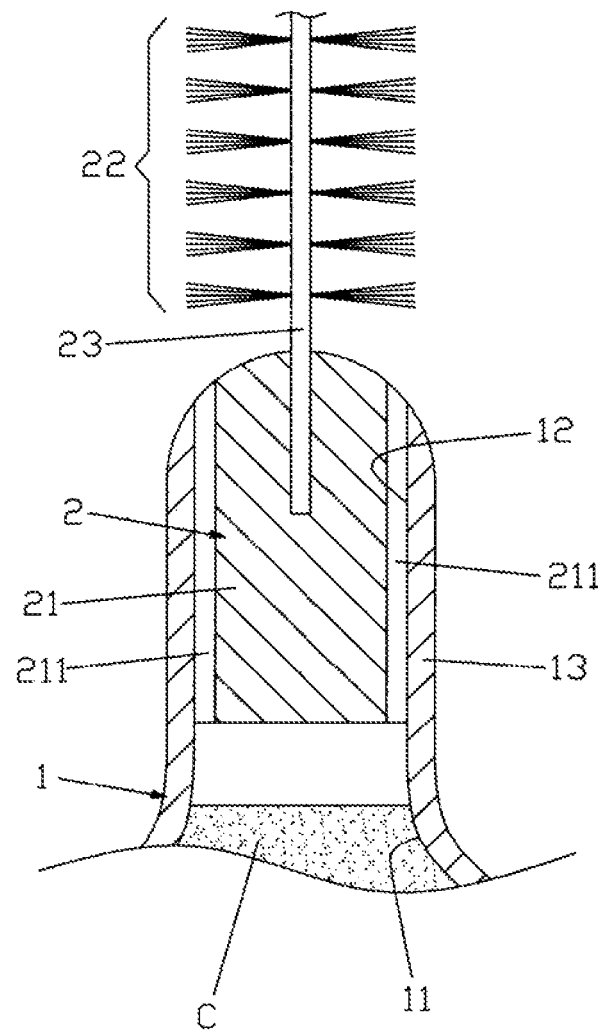
FIG. 5 is an enlarged cross-sectional view of the discharge hole pan of a portable interdental toothbrush in accordance with to the first embodiment of the present invention.

In a portable interdental toothbrush A according to the first embodiment of the present invention, as shown in FIGS. 3-5, there are a cleaning solution tube 1 in which a filling space 11 filled with a cleaning solution C is formed, filling of the cleaning solution C in the filling space 11 is completed, and a discharge hole 12 for discharging the cleaning solution C is formed, and a brush body 2 having a cylindrical fixing portion 21 press-fitted into the discharge hole 12 of the cleaning solution tube 1 formed on one end and a brush 22 attached on the other end, and the fixing portion 21 of the brush body 2 is press-fitted forcibly to the discharge hole 12 of the cleaning solution tube 1.

A main characteristic of the present invention is that, when the discharge hole 12 of the cleaning solution tube 1 is closed by the fixing portion 21 of the blush body 2 while the cleaning solution C is filled in the cleaning solution tube 1, the pressure in the filling space 11 filled with the cleaning solution C becomes lower than the atmospheric pressure; thereby in the case where any external pressure such as pressing the cleaning solution tube 1 by hands is not applied, discharge of the cleaning solution C is prevented and the structure of the portable interdental toothbrush with the cleaning solution is greatly simplified.

In this embodiment, the cleaning solution tube 1 is made of synthetic resins having a property which contracts if pressure is applied by the pressing force like fingers, and restores back if the pressure is removed, wherein the cleaning solution tube 1 is filled with the cleaning solution C in the filling space 11 up to the bottleneck 13 portion in which the discharge hole 12 is formed, and in this state the fixing portion 21 of the brush body 2 is press-fitted.

In this state, since the cleaning, solution C filled in the cleaning solution tube 1 is filled in the filling space 11 and the fixing portion 21 is press-fitted in the discharge hole 12, the pressure inside the filling space 11 is lower than the atmospheric pressure. Accordingly, even if the discharge hole 12 is located on the lower side while the cleaning solution tube 1 is standing upside down, the cleaning solution C inside the cleaning solution tube 1 is not discharged through the discharge hole 12.

In the case where the cleaning solution C needs to be discharged, a pressure is generated inside the filling space 11 filled with the cleaning solution when pressing an outer surface of the cleaning solution tube 1 with the external pressure such as fingers, and the cleaning solution C receives a pressure which is discharged in the direction of the discharge hole 12; thereby the cleaning solution C is discharged through a gap between the fixing portion 21 and the discharge hole 12 by the action of the discharge pressure in the direction of the fixing portion 21 of the brush body 2. If the pressure is not applied by taking the fingers away, the discharge of the cleaning solution C is stopped.

When such an external force is applied, as shown in FIG. 5, a plurality of outflow grooves 211 are formed finely on an outer surface of the fixing portion 21 of the brush body 2 in a longitudinal direction, and the cleaning solution C receiving the discharge pressure is discharged along the outflow grooves 21 to wet the brush 22.

The brush body 2 is configured such that the fixing portion 21 is formed on one end of the brush body 2, the brush 22 for cleaning teeth and gum while contacting with the teeth and gum is attached to the other end, and the fixing portion 21 and the brush 22 are connected with each other via wire 23.

As shown in FIG. 5, since the fixing portion 21 of the brush body 2 is press-fitted to the discharge hole 12 of the cleaning solution tube 1 which is filled with the cleaning solution C, the cleaning solution C is not discharged. However, if a pressure is applied on the outer surface of the cleaning solution tube 1, the pressure affects the cleaning solution C to be discharged through the discharge hole 12, and the cleaning solution C is discharged along the outflow grooves 211 of the fixing portion 21 to the brush 22 in make the portable interdental toothbrush A to be the state of use.

Accordingly, the portable interdental toothbrush A according to the first embodiment of the present invention consists of only a bottle-shaped cleaning solution tube 1, and a brush body 2 in which the fixing portion 21 is formed on one end and the brush 2 is attached to the other end, by using the feature that the discharge of the cleaning solution is prevented by maintaining the filling space of the cleaning solution gibe at a low pressure while using the cleaning solution. Therefore, the structure becomes very simple and so the portable Interdental toothbrush can be simply manufactured, automatic mass production is possible, and the portable interdental toothbrush with the cleaning solution can be provided at a low price.

Figure 6:
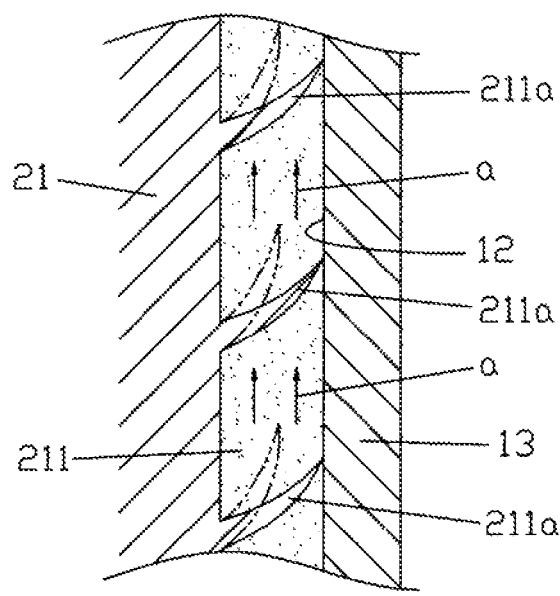
FIGS. 6 and 7 are enlarged cross-sectional view of the discharge hole part of a portable interdental toothbrush in accordance with the second embodiment of the present invention.
Figure 7:
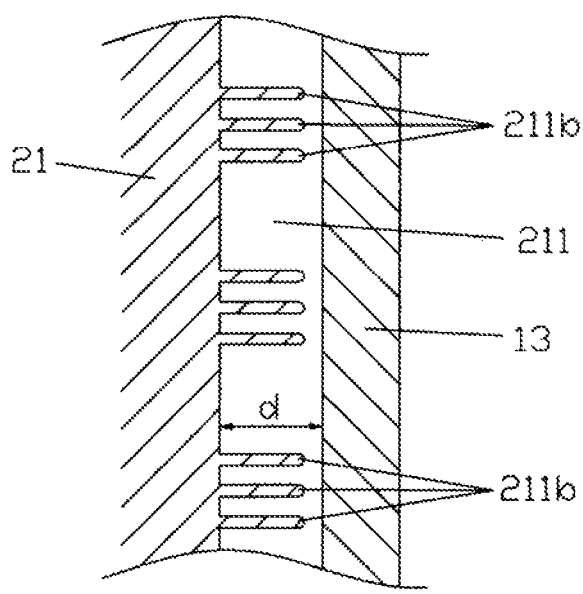

As shown in FIG. 6, a portable interdental toothbrush A according to the second embodiment of the present invention includes a fluidized plate 211a formed on the outer surface of the outflow grooves 211 of the fixing portion 21 of the brush body 2 in a slanted direction to the outside brush 22 to certainly prevent an unintended discharge to the outside. If pressure is applied in the direction of the arrow A, the cleaning solution C pushes the fluidized plate 211a to the position of the two-dot chain line to be discharged. If a pressure is not applied, an end portion of the fluidized plate 211a is in contact with a discharge hole 12 again to prevent the cleaning solution C from discharging. According to the structure suggested as above, an unintended discharge of the cleaning solution C to the outside is certainly prevented. A similar structure is shown in FIG. 7, and it may be suggested that line bristles 211b not longer than the depth d of the outflow grooves 211 of the fixing portion 21 of the brush body 2 are formed in the outflow grooves 211 to block the discharge of the cleaning solution C by the fine bristles 211b. That is, the cleaning solution C is maintained in a state of contact with lower fine bristles 211b and, even if discharged slightly, it is blocked by the upper fine bristles 211b. Accordingly, the discharge of the cleaning solution C is certainly blocked by the fine bristles 211b.

Figure 8:
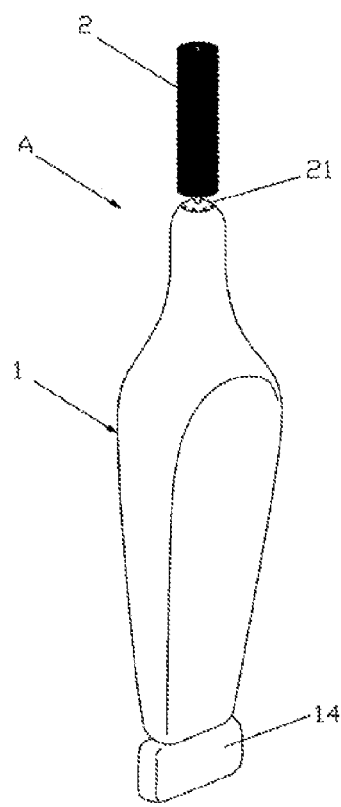
FIG. 8 is a perspective view of a portable interdental toothbrush in accordance with to the third embodiment of the present invention.
Figure 9:
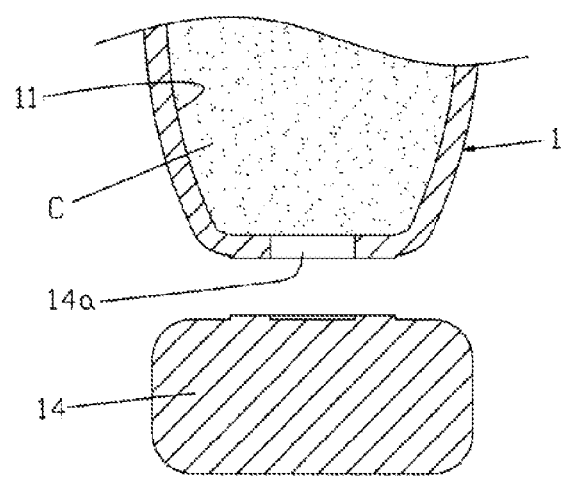
FIG. 9 is a schematic longitudinal cross-sectional view of the portable interdental toothbrush of FIG. 8 in the state that the cutting portion is cut out.

A portable interdental toothbrush A according to the third embodiment of the present invention is configured so as to be used as disposable and comprises, as shown in FIGS. 8 and 9, a cleaning solution tube 1 in which a filling space 11 filled with a cleaning solution is formed, the cleaning solution is filled in the filling space 11, and a discharge hole 12 for discharging the cleaning solution is formed, and a brush body 2 having a cylindrical fixing portion 21 press-fitted to a discharge hole 12 of the cleaning solution tube 1 on one end and a brush 22 attached to the other end, and a the cutting portion 14 which can be cut out is formed on a rear end of the cleaning solution tube 1.

Accordingly, in the present embodiment, the cleaning solution C is filled in the cleaning solution tube 1 close to substantially vacuum state for use as disposable and so discharging to the brush 22 of the brush body 2 is blocked. When cutting out the cutting portion 14 to be used, a perforating hole 14a communicating with the outside is formed on the cut portion to apply a discharge pressure in the cleaning solution tube. Then, if the portable interdental toothbrush A is positioned in which the brush 22 is disposed downward, the cleaning solution C the cleaning solution tube 1 moves downward and flows to the brush 22 through the fixing portion 21 of the brush body 2 to clean the teeth and oral cavity.

Figure 10:
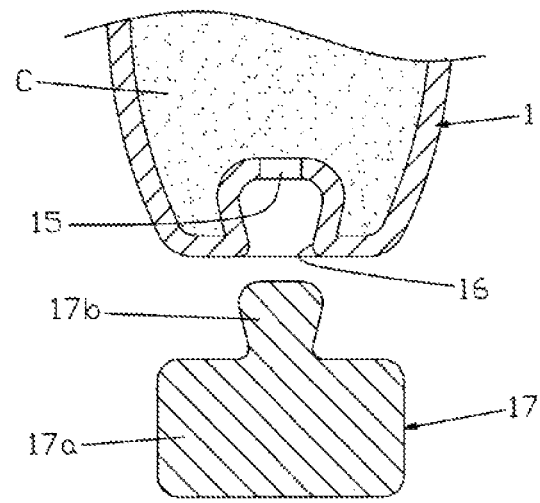
FIG. 10 is a longitudinal cross-sectional view of one end of the portable interdental toothbrush which is assembled detachably according to the fourth embodiment of the present invention.

FIG. 10 illustrates a portable interdental toothbrush A according to the fourth embodiment of the present invention, and the cleaning solution C is filled in the cleaning solution tube 1 close to substantially vacuum state for multiple use and so discharging to the brush 22 of the brush body 2 is blocked. A lower hole 15 is formed on a bottom pail of the cleaning solution tube 1, an engaging protrusion 16 is formed adjacent to the lower hole 15, and an open in and shutting unit 17 made of an elastic material for opening and shutting the lower hole 15 by closely contacting with the lower hole 15 and being caught by the engaging protrusion 16 is fixed detachably. When the user wishes to use the portable interdental toothbrush A, a handle 17a of the opening and shutting unit 17 is rotated orthogonally to make it possible for the contact elastic portion 17b closely adhered to the lower hole 15 to be able to be separated from the engaging protrusion 16, and then the opening and shutting unit 17 is pulled to take the opening and shutting unit 17 away from the lower hole 15 to be separated from the cleaning solution tube 1. Then, air is introduced into the lower hole 15 to discharge the cleaning solution C to the brush 22. Once a certain amount of the cleaning solution is discharged, the lower hole 15 can be closed by assembling die opening and shutting unit 17 to the engaging protrusion 16 again to prevent the cleaning solution C from discharging. The above-described method of separating the opening and shutting unit 17 detachably allows multiple use.

As described above, the portable interdental toothbrush according to the present invention uses the state where the cleaning solution is not discharged to the brush body while the filling space of the cleaning solution tube is maintained to have a low pressure even if the fixing portion of the brush body is inserted and fixed in the discharge hole of the cleaning solution tube filled with the cleaning solution consequently, the portable interdental toothbrush can be manufactured with only two components, the structure becomes simple, and mass production is possible with low cost, thereby allowing consumers to use it at a low price.

Figure 11:
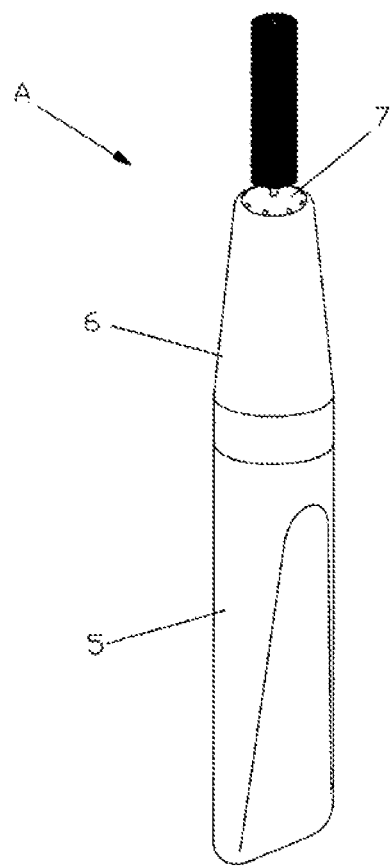
FIG. 11 is a perspective view of a portable interdental toothbrush, in accordance with die fifth embodiment of the present invention.

A portable interdental toothbrush A according to the fifth embodiment of the present invention comprises, as shown in FIG. 11, a cleaning solution tube 5 which receives a cleaning solution to carry it conveniently and has an assembly protrusion 51 for di charging the cleaning solution formed therein, a tube cover 6 assembled to the assembly protrusion 51 of the cleaning solution tube 5, in which an assembly hole 61 into which the assembly protrusion 51 of the cleaning solution tube 5 is inserted and assembled is formed in a lower part, and a fixing hole 62 having a diameter larger than that of the assembly hole into which a brush fixing portion 7 having a brush 71 on one end is formed above the assembly hole 61, and the brush fixing portion 7 in which an insertion end 72 which is inserted and fixed into the fixing hole 62 of the tube cover 6 is formed, a contact end 73 is formed on a free end of the insertion end 72 to be closely attached to the assembly protrusion 51 detachably, and a brush 71 is fixed to the other end.

Figure 12:
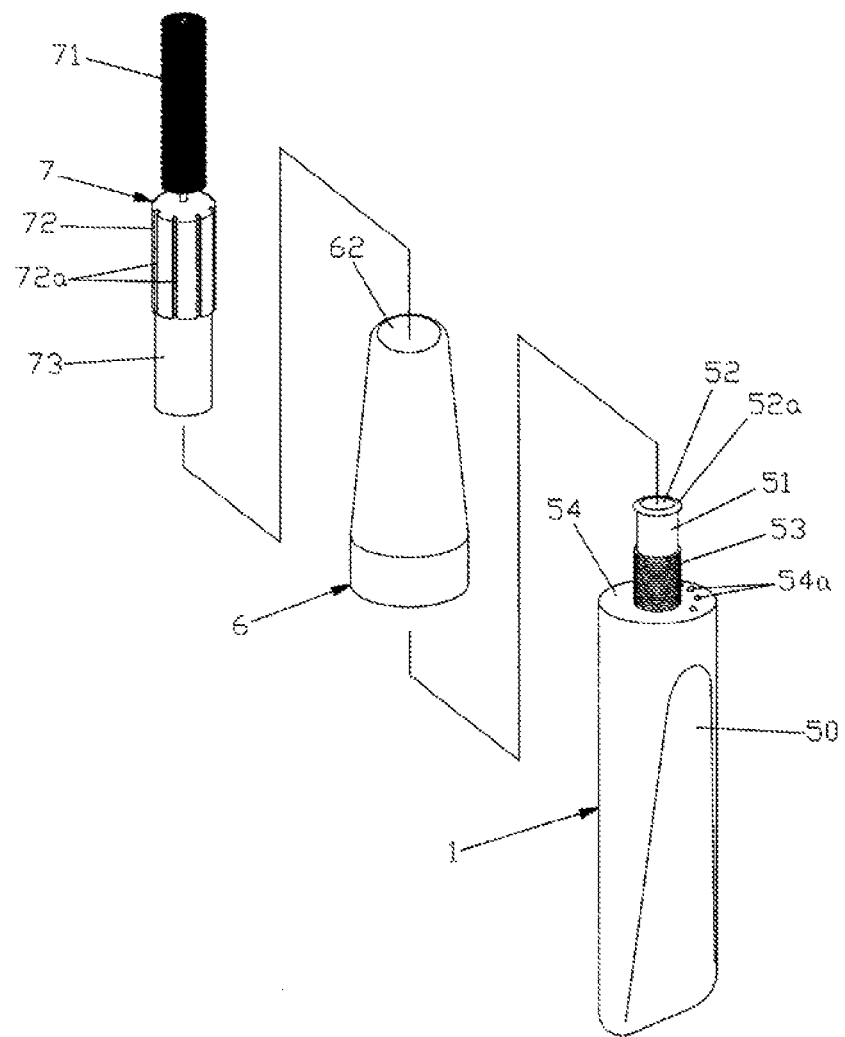
FIG. 12 is an exploded perspective view of a portable interdental toothbrush in accordance with the fifth embodiment of the present invention.
Figure 13:
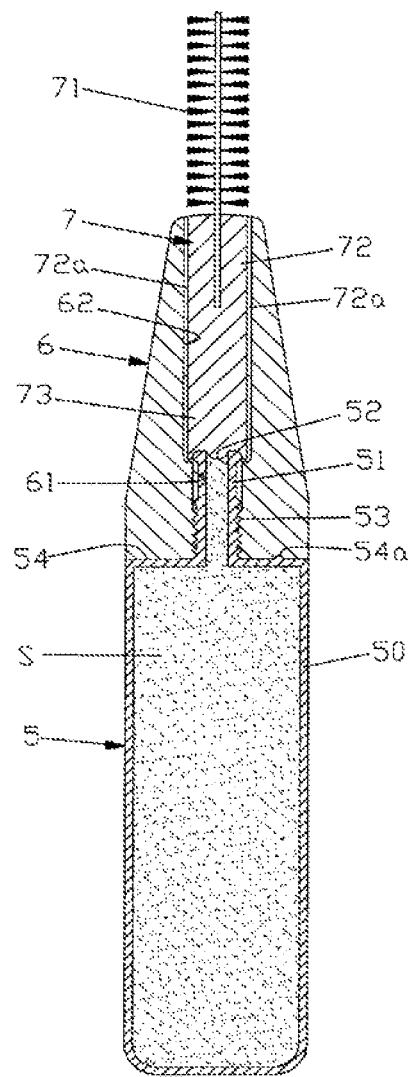
FIG. 13 is a schematic longitudinal cross-sectional view of a portable interdental toothbrush in accordance with the fifth embodiment of the present invention.
Figure 14:
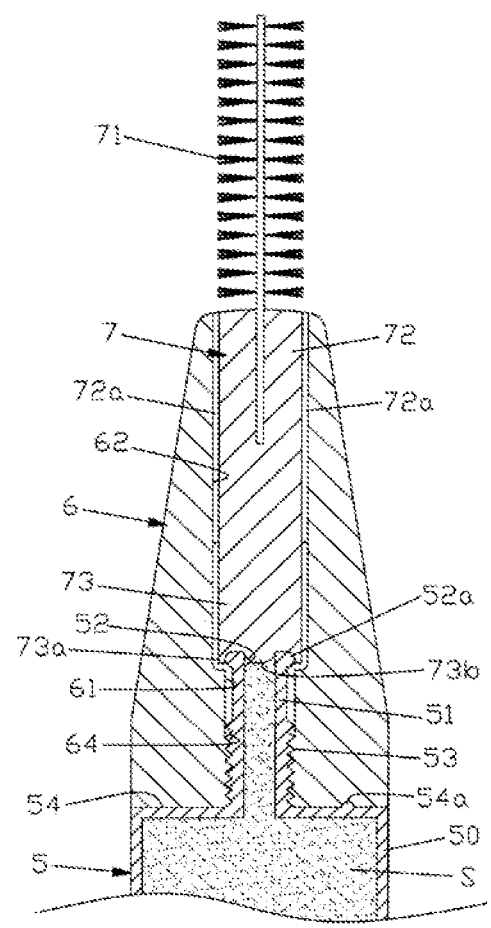
FIGS. 14 and 15 are longitudinal cross-sectional views of a portable interdental toothbrush in accordance with the fifth embodiment of the present invention when the cleaning solution is either blocked or supplied, respectively.
Figure 15:
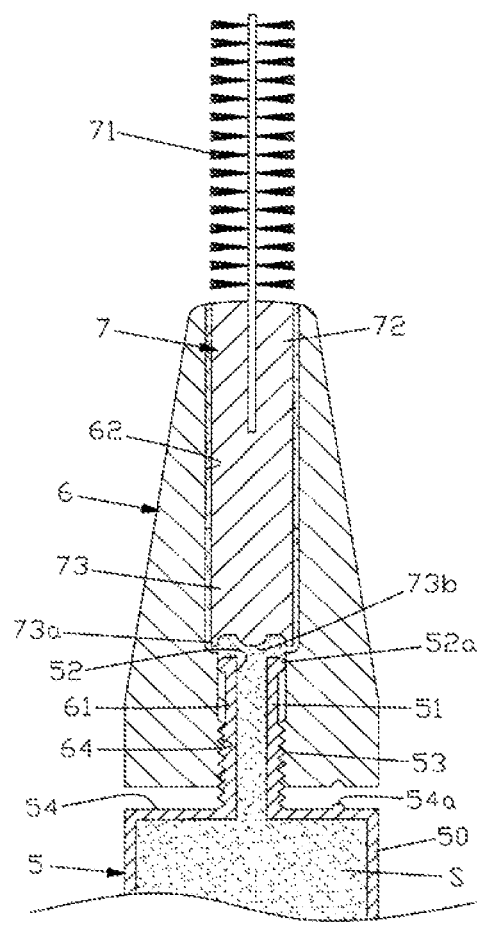

In the cleaning solution tube 5, as shown in FIG. 12, a tube body 50 made of synthetic resins for easy manufacture for receiving a cleaning solution S and an assembly protrusion 51 having a diameter smaller than that of the tube body 50 to form a bottleneck portion extended from the tube body 50 in which a discharge hole 52 for discharging the cleaning solution S is formed on a tip, an assembling screw portion 53 is formed on a lower outer portion, and an assembly protrusion 51 having a radius smaller than that of the tube body 50 are protruded.

In order to prevent damage, reinforced rim 52a is formed thickly on the tip in which the discharge hole 52 of the assembly protrusion 51 is formed, thus reinforcing the strength of the discharge hole.

In this embodiment, an engaging pan 54 is formed on a boundary to the tube body 50 under the assembly protrusion 51, a plurality of protrusions 54a are formed on the engaging part 54, positions of the protrusions 54a are different, and the assembled state with the brush fixing portion 7 is varied depending on the positions of the protrusions 54a, thereby identifying the assembled state with the brush fixing portion 7 easily.

In the tube cover 6, an assembly hole 61 into which the assembly protrusion 51 of the cleaning solution tube 3 is inserted and assembled is formed in a lower portion, and a negative screw portion 64 to be engaged and screw-coupled to the assembling screw portion 53 is formed inside the lower portion of the assembly hole 61 to be screw-coupled with the cleaning solution tube 5.

A fixing hole 62 having a radius larger than that of the assembly hole is formed above the assembly hole 61 of the tube cover 6, an insertion end 72 of the brush fixing portion 7 is inserted and fixed in the fixing hole 62, and a contact end 73 which is a free end of the insertion end 72 is protruded inside the fixing hole 62. A plurality of outflow grooves 72a are formed on an outer surface of the insertion end 72 in a longitudinal direction for the cleaning solution S to outflow along the outflow grooves 72a to be provided to the brush 71. The outflow grooves 72a are formed to have a depth of about 0.05~1 mm.

Figure 16:
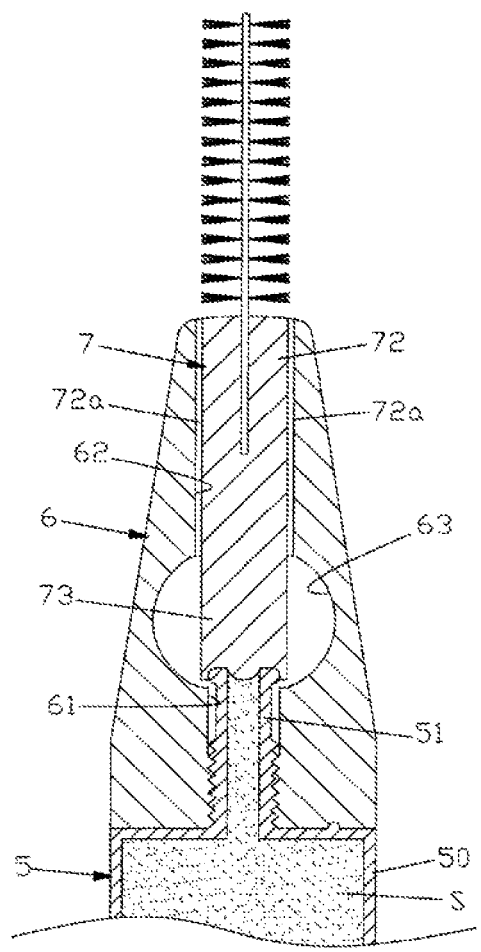
FIGS. 16 and 17 are longitudinal cross-sectional views of a portable interdental toothbrush according to the sixth embodiment of the present invention when the cleaning solution is either blocked or supplied, respectively.
Figure 17:
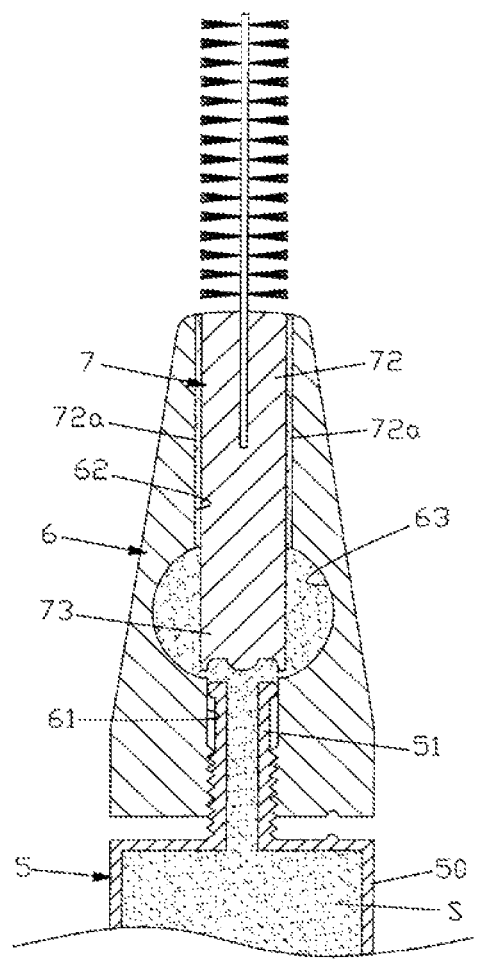

In this embodiment, the tube cover 6 comprises two components of the lower assembly hole 61 and the upper fixing hole 62. However, as shown in FIGS. 16 and 17, an expanded space 63 having a larger radius can be formed between the lower assembly hole 61 and the upper fixing hole 62 of the tube cover 6. This makes the contact end 73 which is a free end of the insertion end 72 to be placed inside the expanded space 63.

In this embodiment, an edge protrusion 73a extended to surround the assembly protrusion 51 of the cleaning solution tube 5 is conned on the contact end 73 of the brush fixing portion 7 and a central protrusion 73b inserted in the discharge hole 52 is formed to prevent the cleaning solution S from discharging certainly. Accordingly, the discharge of the cleaning solution is prevented while the contact end 73 of the brush fixing portion 7 and the assembly protrusion 51 of the cleaning solution tube 5 are closely adhered to each other. Meanwhile, the close adhesion end 73 of the brush fixing portion 7 and the assembly protrusion 51 of the cleaning solution tube 5 are spaced apart, the cleaning solution S is discharged through the spaced gap and supplied to die brush 71.

In another embodiment in which the expanded space 63 having a radius larger than that of the fixing hole 62 is formed between the lower assembly hole 61 and the upper fixing hole 62 of the tube cover 6 and the close adhesion end 73 which is a free end of the insertion end 72 is placed inside the expanded space 63, the elastic contact end 73 of the brush fixing portion 7 goes beyond the fixing hole 62 and is placed in the expanded space 63 wider than the fixing hole 62 to surround the edge of the assembly protrusion 51 of the cleaning solution tube 5 more widely, thereby controlling the discharge of the cleaning solution S more positively.

The operation of the portable interdental toothbrush A according to the present invention having the above configuration is described below.

To use the portable interdental toothbrush A according to the present invention, if the cleaning solution tube 5 is turned in an open direction in the state that the discharge of the cleaning solution S is prevented by the close adhesion of the close adhesion end 73 of the brush fixing portion 7 and the assembly protrusion 51 of the cleaning solution tube 5, screw-coupling, of the assembling screw portion 53 of the cleaning solution tube 5 and the negative screw portion 64 of the tube cover 6 which are screw-coupled is released to open a gap between the cleaning solution tube 5 and the tube cover 6. Then, the close adhesion of the edge protrusion 73a of the contact end 73 surrounding and closely adhered to the assembly protrusion 51 of the cleaning solution tube 5 is naturally released and, at the same time, inserted into the discharge hole 52 of the cleaning solution tube 5 to release the close adhesion of the central protrusion 73b with the discharge hole 52 as well. As a result, a gap is generated between the assembly protrusion 51 and the contact end 73, and the cleaning solution S is discharged through the generated gap and provided to the brush 71 along the outflow grooves 72a to use the portable interdental toothbrush A with the cleaning solution supplied.

When the use of the portable interdental toothbrush A is completed, turn the cleaning solution tube 5 in the opposite direction. Then, screw-coupling of the assembling screw portion 53 of the cleaning solution tube 5 and the negative screw portion 64 of the tube cover 6 which are screw-coupled is tighten again, and the gap between the cleaning solution tube 5 and the tube cover 6 becomes narrower. Subsequently, the gap is removed naturally, and the assembly protrusion 51 of the cleaning solution tube 5 and the edge protrusion 73a of the close adhesion end 73 which were moved apart adhere closely again, and, at the same time, the central protrusion 73b is inserted into and contacted with the discharge hole 52 of the cleaning solution tube 5. Consequently, the discharge of the cleaning solution S is blocked. Accordingly, it can be used conveniently and the manufacturing becomes easy due to the simple structure. Manufacturing costs of the interdental toothbrush are low, which allows a lot of users to purchase and use for maintenance of good oral health.

It is possible to manufacture the same products as the portable interdental toothbrush in accordance with the present invention repeatedly in the manufacturing field of the interdental, toothbrush. Accordingly, the present invention possesses industrial usability.

Although the specific embodiments of the present invention have been disclosed for illustrative purposes, those skilled in the art will appreciate that various modifications, additions and substitutions can be made to the invention without departing from the scope and spirit of the invention as disclosed in the accompanying claims.

What is claimed is:

1. A portable interdental toothbrush (A) which comprises:
    a cleaning solution tube (5) in which a cleaning solution is received to be carried conveniently and an assembly protrusion (51) for discharging the cleaning solution is formed;
    a tube cover (6) assembled detachably to the assembly protrusion (51) of the cleaning solution tube (5), in which an assembly hole (61) into which the assembly protrusion (51) of the cleaning solution tube (5) is inserted and assembled is formed on one end, and a fixing hole (62) having a diameter larger than that of the assembly hole (61) is formed on the other end; and
    a brush fixing portion (7) having an insertion end (72) inserted into the fixing hole (62) of the tube cover (6) and fixed, a protruded close adhesion end (73) formed on a free end of the insertion end (72) to be contacted detachably to the assembly protrusion (51), and a brush (71) fixed at the other end thereof,
    wherein an edge protrusion (73a) extended to wrap up the assembly protrusion (51) of the cleaning solution tube (5) is formed on the protruded close adhesion end (73) of the brush fixing portion (7).

2. The portable interdental toothbrush of claim 1, wherein the cleaning solution tube (5) is made of synthetic resins to make its manufacturing convenient and comprises a tube body (50) in which a cleaning solution (S) is received, a discharge hole (52) for discharging the cleaning solution (S) formed on a tip of the assembly protrusion (51) which is a bottleneck portion extended from the tube body (50), and an assembling screw portion (53) formed outside a lower portion of the assembly protrusion (51).

3. The portable interdental toothbrush of claim 1, wherein a central protrusion (73b) which is inserted into and contacted detachably to a discharge hole (52) is formed on the protruded close adhesion end (73) of the brush fixing portion (7), the discharge hole (52) for discharging a cleaning solution (S) being formed on a tip of the assembly protrusion (51).

4. The portable interdental toothbrush of claim 1, wherein:
    an expanded space (63) having a radius larger than that of the fixing hole (62) is formed between the fixing hole (62) and the assembly hole (61) of the tube cover (6); and
    the protruded close adhesion end (73) which is a free end of the insertion end (72) is disposed inside the expanded space (63).

* * * * *